United States Patent [19]
Lawin et al.

[11] Patent Number: 5,808,081
[45] Date of Patent: Sep. 15, 1998

[54] CHICHIBABIN AMINATIONS OF PYRIDINE BASES

[75] Inventors: Phillip B. Lawin, Indianapolis, Ind.; Angela R. Sherman, Baltimore, Md.; Martin P. Grendze, Indianapolis, Ind.

[73] Assignee: Reilly Industries, Inc., Indianapolis, Ind.

[21] Appl. No.: 765,281
[22] PCT Filed: Jun. 26, 1995
[86] PCT No.: PCT/US95/08030
§ 371 Date: Dec. 20, 1996
§ 102(e) Date: Dec. 20, 1996
[87] PCT Pub. No.: WO96/00216
PCT Pub. Date: Jan. 4, 1996
[51] Int. Cl.$^6$ ............. C07D 213/72; C07D 213/127
[52] U.S. Cl. ................. 546/304; 546/250; 546/251
[58] Field of Search ................ 546/250, 251, 546/304

[56] References Cited

U.S. PATENT DOCUMENTS 4,386,209  5/1983  McGill et al. ............ 546/311
4,405,790  9/1983  McGill et al. ............ 546/304

*Primary Examiner*—Alan L. Rotman
*Attorney, Agent, or Firm*—Woodard, Emhardt, Naughton, Moriarty & McNett

[57] ABSTRACT

Improved Chichibabin aminations of pyridine bases are described which are conducted under a pressurized gas phase containing ammonia and in the presence of a selected additive which increases the reaction rate, and also in preferred processes favorably alters the isomer ratios and product yields from the aminations while benefiting product workup and recovery as well.

31 Claims, No Drawings

CHICHIBABIN AMINATIONS OF PYRIDINE BASES

CROSS-REFERENCE

This application is a 371 of PCT/U.S. 95/08030 filed Jun. 26, 1995.

BACKGROUND OF THE INVENTION

This invention relates generally to the amination of nitrogen-containing heterocycles by alkali metal amides, and in particular to an improved Chichibabin amination of pyridine bases.

In 1914, Chichibabin and Seide first reported that 2-methylpyridine, or more commonly alpha-picoline, underwent direct amination in the free alpha-position on the ring when treated with sodium amide in toluene at elevated temperatures. Chichibabin and Seide, *J. Russ. Phys. Chem. Soc.*, 46, 1216 (1914). This reaction was later extended by Chichibabin and his contemporaries to amination of many pyridine, quinoline and isoquinoline bases. It has since been recognized as one of the more important and influential developments in pyridine chemistry, so much so that the reaction itself has become synonymous with the name of its discoverer. Its commercial importance should also not be discounted as, for example, the 2-amino amination product of pyridine itself has become an enormously important and useful starting material for further synthesis in many areas.

The Chichibabin reaction has been the subject of much study and comment through the years, both as to scope and as to the mechanism of the amination. For example, although first carried out in toluene, the reaction has since been carried out in other aprotic solvents of which dialkylanilines, liquid paraffin and other hydrocarbons such as benzene, xylene, cumene, mesitylene and petroleum fractions are most common. Similarly, although first accomplished using sodium amide, or more commonly sodamide, the reaction has since been carried out with other metal amides such as potassium amide, barium amide, etc., particularly when using low temperatures and long reaction times in attempting to slow the reaction to study the mechanism of its amination process. The Chichibabin mechanism remains one of the least understood substitution reactions in heterocyclic chemistry owing to the difficulty in handling the alkali metal amides and in studying kinetics of a process which takes place under heterogeneous conditions at high temperatures. Classically, those conditions have included heating the mixture at atmospheric pressure and at temperatures between about 100°–200° C. Another characteristic feature has been the evolution of hydrogen gas and ammonia gas which signals the start of the reaction and identifies its progress toward completion. Novikov, Pozharskii & Doron'kin, Translated from *Khim. Geterotsikl. Soedin.*, No. 2, 244 (1976); Levitt & Levitt, *Chem. & Ind.*, 1621 (1963).

The base compound which undergoes amination has also received much study. Reports document the amination of mono and diazines such as pyridines, quinolines, isoquinolines, benzoquinolines, phenanthridines, acridines, benzimidazoles, quinazolines, naphthyridines, pyrimidines, pyrazines and other heterocyclic systems. Reactions related to the Chichibabin amination have also been studied which are not heterocycles, but have a N=CH group such as Schiff bases. Pozharskii, Simonov and Doron'kin, *Russ. Chem. Rev.*, 47, 1042 (1978), Translated from *Uspekhi Khim.*, 47, 1933 (1978). The result of these efforts is that the predictability of Chichibabin aminations is thought to be high for a given base compound, as are the expected product or products of the reaction. Although such certainty is helpful, situations arise where a partial or complete change in the Chichibabin result is desirable. For example, expected products may not be desired, or new products may be wanted, or isomer ratios may be preferably reversed.

An important example of this last category is the case of 3-substituted pyridine bases, and particularly 3-alkyl derivatives, which in early work were reported to undergo Chichibabin amination to produce predominantly 2-amino-3-alkylpyridine ("2,3-isomer") and to a much lesser extent 2-amino-5-alkylpyridine ("2,5-isomer"). The amination of 3-methylpyridine, also known as beta-picoline, is an excellent example, which in early reports yielded the 2,3- and 2,5-isomers in a ratio of about 10.5:1. Abramovitch, *Advan. Heterocvcl. Chem.*, 6, 294 (1966); Abramovitch, Helmer and Saha, *Chem. & Ind.*, 659 (1964); Abramovitch, Helmer and Saha, *Can. J. Chem.*, 43, 727 (1965).

U.S. Pat. No. 4,386,209 describes a significantly improved Chichibabin reaction which provides high 2,5-:2,3- isomer ratios. The improved reactions are conducted under a pressurized, ammonia-containing gas phase which is shown to favorably alter the isomer ratios obtained from the Chichibabin reaction and enable an increased production of the 2,5- isomer. Nonetheless, the reaction rates resultant of the described processes are fairly slow, and handling of the reaction mixture after hydrolysis is complicated by a substantial froth or emulsion/particulate layer.

In light of the above background, there remain areas in which Chichibabin aminations would desirably be improved, for example relating to obtaining increased reaction rates while not compromising acceptable yields, and to simplifying product work up. The present invention addresses these needs

SUMMARY OF THE INVENTION

Accordingly, provided by the present invention is an improved Chichibabin amination of a pyridine base in which increased reaction rates and other advantages are obtained. For example, aminations of pyridine bases are provided in which increased reaction rates are obtained while not compromising and in some cases improving the yield of desired products and/or selectivities. Preferred Chichibabin aminations of the invention involve reacting a reaction mixture containing an organic solvent, a pyridine base, sodamide, and an organic additive compound which increases the rate of said reacting and is encompassed by the formula:

I wherein X is S, O, NR$^3$, or CO$_2$ wherein R$^1$, R$^2$ and R$^3$ are H, alkyl, aryl, or aralkyl, and n is 0 to about 12;

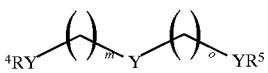

II wherein Y is O, S, or NR$^6$, R$^4$, R$^5$ and R$^6$ are H, alkyl, aryl, or aralkyl, and m and o are 1 to about 12;

III wherein Z is C or S, A is O or NR$^9$, and R$^7$, R$^8$ and R$^9$ are H, alkyl, aryl or aralkyl;

IV wherein B is $OR^{11}$, $NR^{12}R^{13}$, $SR^{14}$, $CO_2R^{15}$, $NO_2$ or CN, $R^{10}$ is alkyl, and $R^{11}$, $R^{12}$, $R^{13}$, $R^{14}$ and $R^{15}$ are H, alkyl, aryl or aralkyl;

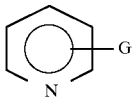
V wherein G is $-OR^{16}$, $-ROR^{17}$ or $NR^{22}R^{23}$ wherein $R^{16}$ and $R^{17}$ are H or alkyl, and R, $R^{22}$ and $R^{23}$ are alkyl;

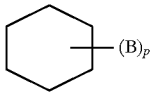
VI wherein B is as defined above and p is 1 to 4;

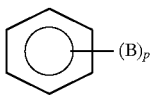
VII wherein B is as defined above and p is 1 to 4; or
is a cyclic ether or single electron transfer agent, so as to aminate said base. The preferred reactions are conducted in a solid liquid heterogeneous reaction mixture in the presence of a selected additive and under an ammonia-containing gas phase at a superatmospheric pressure. In particularly preferred embodiments of the invention, the additive(s) include hydroxyalkylamino compounds of the formula $(R^{18})(R^{19})N-R^{20}$ wherein $R^{18}$ and $R^{19}$, which may be the same or may differ one from the other, are —H, lower alkyl or hydroxy-substituted lower alkyl, and $R^{20}$ is hydroxy-substituted lower alkyl.

In one of its preferred forms, the invention thus provides an improved Chichibabin amination which comprises reacting a reaction mixture containing a pyridine base, sodamide, and an additive as identified, and an organic solvent, to aminate the pyridine base, the reacting being under a gas phase at a pressure of at least about 50 psi, the gas phase containing ammonia at a partial pressure of at least about 5 psi.

In another preferred form, the invention provides a process for producing an aminated pyridine base, in which a reaction mixture is formed containing a pyridine base, sodamide, and an additive as identified above, and reacting the reaction mixture to produce an aminated pyridine base. During the reaction, an ammonia-containing gas phase at superatmospheric pressure is maintained above the reaction mixture. The additive will be present in an amount which is effective to increase the rate of reaction (i.e. increased relative to that which would be obtained without the additive). The reaction mixture is then hydrolyzed, and the aminated pyridine base so formed is then recovered.

In another preferred form, the invention provides a process for increasing the rate of reaction in a Chichibabin amination. The process includes conducting the Chichibabin amination in a heterogeneous reaction mixture containing sodamide, a pyridine base, one or more of the above-noted additives, and an organic solvent, the reaction mixture being exposed during the amination to a nitrogen-containing gas phase at superatmospheric pressure.

The invention also provides a preferred Chichibabin amination of a pyridine base with sodamide in the presence of an organic solvent, wherein the amination is conducted in the presence of one ore more of the above-noted additives and of a gas phase at superatmospheric pressure and containing a partial pressure of ammonia substantially equal to or greater than the autogenous pressure of ammonia generated by the reaction.

The amination reactions of the above-described embodiments of the invention are desirably conducted in a substantially inert atmosphere at temperatures between about 100°–250° C. and without refluxing the mixture as is common in the classic Chichibabin reaction. The added ammonia may be injected in gaseous form, or left as liquid ammonia in the reaction mixture as when sodamide is prepared in situ by reacting sodium in excess liquid ammonia prior to conducting the amination. The temperature and pressure in the vessel are preferably maintained for a period sufficient to cause substantial amination to occur as measured by the production of hydrogen gas by the reaction, although both may vary from their initial settings. For example, temperature is preferably maintained between about 130°–200° C. whereas reaction pressures of at least about 300 psi are preferred with at least about 15–100 psi of ammonia being initially present. The autogenous pressure of gases evolved during amination can be used to pressurize the reaction vessel, and excess gases can be vented off to prevent too much build up.

Preferred processes of the invention also involve the presence of an aminopyridine in the reaction mixture, more preferably one or more of the desired products of the reaction, e.g. 2-amino-5-lower alkyl pyridine.

Additional preferred embodiments, features and advantages of the present invention will be apparent from the description which follows.

DESCRIPTION

For the purpose of promoting an understanding of the principles of the invention, reference will now be made to the several embodiments thereof and specific language will be used to describe the same. It will nevertheless be understood that no limitation of the scope of the invention is thereby intended, such alterations and further modifications, and such further applications of the principles of the invention therein being contemplated as would normally occur to one skilled in the art to which the invention relates.

A feature of the present invention is the discovery that significant and surprising results were achieved by the inclusion in a Chichibabin amination of a pyridine base of one or more organic additive compounds encompassed by the formula:

I wherein X is S, O, $NR^3$, or $CO_2$ wherein $R^1$, $R^2$ and $R^3$ are H, alkyl, aryl, or aralkyl, and n is 0 to about 12;

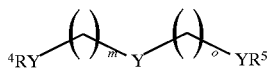
II wherein Y is O, S, or $NR^6$, $R^4$, $R^5$ and $R^6$ are H, alkyl, aryl, or aralkyl, and m and o are 1 to about 12;

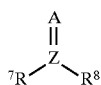
III wherein Z is C or S, A is O or $NR^9$, and $R^7$, $R^8$ and $R^9$ are H, alkyl, aryl or aralkyl;

IV wherein B is $OR^{11}$, $NR^{12}R^{13}$, $SR^{14}$, $CO_2R^{15}$ $NO_2$ or CN, $R^{10}$ is alkyl, and $R^{11}$, $R^{12}$, $R^{13}$, $R^{14}$ and $R^{15}$ are H, alkyl, aryl or aralkyl;

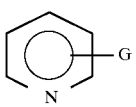

V wherein G is —OR$^{16}$, —ROR$^{17}$ or NR$^{22}$R$^{23}$ wherein R$^{16}$ and R$^{17}$ are H or alkyl and R, R$^{22}$ and R$^{23}$ are alkyl;

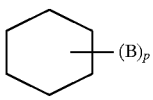

VI wherein B is as defined above and p is 1 to 4;

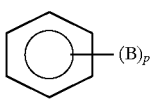

VII wherein B is as defined above and p is 1 to 4; or
is a cyclic ether or single electron transfer agent, so as to aminate said base.

In the above formulas, "alkyl" refers to alkyl groups having from 1 to about 12 carbon atoms, and typically preferred alkyl groups are lower alkyl, i.e. having from 1 to about 5 carbon atoms. The term "aryl" refers to mono- or polycyclic aromatic compounds, preferably having up to about 30 carbon atoms. Preferred aryl groups include phenyl and napthyl groups. The term "aralkyl" refers to groups of the formula -alkyl-aryl, for example benzyl groups.

As regards additives of Formula (I) above, preferred compounds occur where n is 1 to about 6, and wherein the "R" groups present (i.e. R$^1$, R$^2$, etc.) are either H or lower alkyl. Additives of Formula II preferably also have "R" groups which are —H or lower alkyl, and further at least one of m and n is preferably at least 1. Preferred values for m and n are 0 to 6. Preferred Formula III additives occur where the "R" groups are lower alkyl or phenyl, and wherein Z is C and A is O. Formula IV additives are preferred wherein the "R" groups are H or lower alkyl groups, and conveniently can include lower alkylamines and lower alkanols. The pyridine compounds of Formula V are also preferred where the "R" groups are H or lower alkyl, with hydroxyl-containing pyridine compounds demonstrating advantage as shown in the Examples below. Formula VI and VII additives occur with preference wherein p is 2 and wherein the substituents B occur immediately next to one another on the ring (i.e. in the ortho-configuration) although meta- and para-configurations will also be suitable. A variety of cyclic ethers, for example including relatively large ethers such as 18-crown ethers, are also suitable additives for the present invention, as are the so-called single electron transfer agents such as cumene, diphenylketone, and the like. Other various compounds which increase the rate of reaction are also suitable, and include for instance HMPA (hexamethylphosporamide), tetramethylammonium acetate (TMA), and 1-hexyne.

In this regard, a preferred group of additives from work to date includes hydroxyalkylamine compounds of the formula (R$^{18}$) (R$^{19}$)N—R$^{20}$ wherein R$^{18}$ and R$^{19}$, which may be the same or may differ one from the other, are —H, lower alkyl or hydroxy-substituted lower alkyl, and R$^{20}$ is hydroxy-substituted lower alkyl. The additive is preferably incorporated in the reaction mixture in a molar ratio of about 0.001 to about 0.2 relative to pyridine base, and more preferably such molar ratio is about 0.02 to about 0.08. These amounts will effectively increase the rate of the Chichibabin amination at hand, and, correspondingly, decrease the reaction time to completion. In this regard, the applicants have found that in preferred reactions the incorporation of the additive can decrease the reaction time 10% or more relative to corresponding reactions in which the additive is not included. Substantial decreases in reaction times, as achieved by the present invention, provide enormous advantage in commercial settings, for example improving production capacities and thus reducing production costs. In addition, the applicants have discovered that the inclusion of the additive in the Chichibabin amination of 3-lower alkyl pyridines substantially improves yields of the 2,5- isomer as well as the 2,5-:2,3- isomer ratios, and in the case of hydroxyalkylamines such as monoethanolamine also improves the color of the reaction mix after hydrolysis, and alleviates frothing or emulsion problems which can be encountered in product separations following reactions not employing the hydroxyalkylamine.

In a preferred mode of operating an inventive amination, after the reactants and hydroxyalkylamine are combined in a pressure vessel, the gas phase above the mixture is initially pressurized to at least about 50 psi and ammonia added to the vessel sufficient to produce an initial partial pressure of ammonia of at least about 5 psi in this gas phase. The mixture is heated to a temperature sufficient to cause amination to proceed, and pressure is maintained at or above this initial 50 psi level during the course of the reaction until hydrogen evolution has substantially ceased. Although the autogenous pressure of gases evolved in situ during amination can be used to assist in maintaining pressure during the reaction, it is preferred to initially purge the vessel of air and pressurize it using an inert gas such as nitrogen, argon, etc., and then to conduct the amination in the substantially inert nitrogen atmosphere. In this regard, the term "substantially" is meant to define the condition that develops during amination in which evolved hydrogen and possible other gases enter the gas phase resulting in a predominant, but not totally inert nitrogen atmosphere.

More preferably, an initial ammonia pressure of at least about 15–100 psi is in the gas phase, most preferably in the range of 40–50 psi. As the amination proceeds, some ammonia may be lost in venting off excess pressure due to hydrogen and other gases being evolved without detracting from the results of the reaction. This depends, of course, upon the size and efficiency of the pressure vessel and condenser used.

In one mode of carrying out the invention, sodamide is prepared in situ in the reactor by reacting sodium with excess liquid ammonia. After sodamide formation, a portion of the liquid ammonia is removed and an organic solvent added to the same vessel. The pyridine base and hydroxyalkylamine additive are then combined in the vessel. Enough liquid ammonia is left in the reactor so that when the mixture was brought to a temperature sufficiently high to cause amination to begin, a partial pressure of the remaining ammonia in the gas phase is provided sufficient to achieve the desired levels. Compounds which dissociate into free ammonia can also be provided to the reaction mixture to provide the ammonia source. More preferably, however, gaseous ammonia is directly injected into the vessel during pressurizing of the gas phase.

As to other conditions of the reaction, after bringing the mixture to a temperature sufficiently high to cause hydrogen evolution (and thus amination) to begin, the reaction mixture is maintained at a temperature sufficiently high to cause, or to permit, substantial amination to take place. A temperature range of between about 100°–250° C. is preferred, while most preferred is a range of about 130°–200° C. In addition, it has proven advantageous to conduct the initial stages of the reaction at a relatively lower temperature within this range, and the latter stages of the reaction at a relatively higher temperature within this range. Such temperature steps during the reaction have maintained advantageously high 2,5-:2,3- isomer ratios in the amination of 3-alkyl pyridines, while allowing the completion of the reaction more quickly.

As to the organic solvent, lower alkyl benzenes, for example toluene and xylene, are preferred, although other organic solvents may also be used. Many such solvents are common to Chichibabin aminations.

Aminations of the present invention can be applied to a broad variety of pyridine bases, which for purposes herein include both substituted and unsubstituted pyridine bases. In addition, pyridine base as used herein also includes benzo derivatives of pyridine bases such as quinolines and isoquinolines. In this regard, a variety of suitable substituted and unsubstituted pyridine bases are known, and their utilization in the present invention will be well within the purview of those skilled in the pertinent art.

The preferred amination of the present invention is applied to a 3-lower alkyl pyridine. In this regard, the term "lower alkyl" as used herein intends a branched or unbranched alkyl group having 1 to 5 carbon atoms. Thus, preferred substrates for amination will include 3-methylpyridine, 3-ethylpyridine, 3-propylpryidine, 3-isopropylpyridine, 3-butylpyridine (all butyl isomers), and 3-pentylpyridine (all pentyl isomers). Most preferred to date is 3-methylpyridine.

Advantageous reactions of the invention can be conducted by adding an amount of pyridine base and the additive to a pressure vessel such as an autoclave in which sodamide has been preformed in at least a slight stoichiometric excess relative to the pyridine base. This addition step can be carried out at room temperature and with the prior addition of an organic solvent and optionally a dispersing agent such as oleic acid. The vessel is then sealed, purged of air with nitrogen, and pressurized to about 45 psi with gaseous ammonia and to about 300 psi with nitrogen in the gas phase above the solid liquid heterogeneous reaction mixture. The vessel and its contents are heated rapidly with stirring to between about 130°–200° C. at which time evolution of hydrogen gas begins, signaling the start of amination. The pressure in the vessel will generally increase because of this temperature rise and because of gas evolution even without further pressurizing with nitrogen gas. The temperature is preferably maintained in the 130°–200° C. range and the pressure maintained between about 300–1000 psi as a commercially practicable range, with about 350 psi being most preferred, until hydrogen evolution substantially ceases, signaling the completion of the amination. Excess pressure can be vented off during the reaction through a pressure relief valve or other means. At the end of the amination, the vessel can be allowed to cool to room temperature and vented to atmospheric pressure. The reaction mixture can then be hydrolyzed and removed, and the products of the reaction isolated using standard procedures.

An aminopyridine catalyst is also preferably included in the reaction mixture prior to pressurizing the vessel to help initiate the reaction and encourage formation of the desired product or products. Preferably, the aminopyridine catalyst will be one or more of the desired products of the reaction, e.g. a 2-amino-3-lower alkyl pyridine or a 2-amino-5-lower alkyl pyridine, or a mixture thereof. The catalyst or catalyst mixture can be, for example, a portion of the reaction products of a previous amination which is not isolated but rather left in the reactor to serve a catalytic function in the subsequent amination. Moreover, the other additives identified herein can be used in combination with one another to achieve still more beneficial properties in the amination reactions.

To promote a further appreciation and understanding of the present invention, the advantages it provides, and preferred modes of operation, the following specific examples are provided. It will be understood that these examples serve to illustrate the invention, and are not limiting in nature. In these examples as in the entire specification and the claims which follow, temperatures are given in degrees centigrade (°C.) and pressures are given in pounds per square inch gauge (psig) unless otherwise stated. In addition, the following abbreviations are used: mol=moles; Tol=toluene; MEA=monoethanolamine; Vol=volume; Temp= temperature; T=time and is given in minutes unless otherwise noted; Rxn=reaction; Press=pressure; mL=milliliters; L=liters; GC=gas chromatography; 2A5=2-amino-5-methylpyridine; 2A3=2-amino-3-methylpyridine.

EXAMPLES 1–2

Amination of 3-picoline in the presence of monoethanolamine (MEA)

In a one liter, 3 neck flask, equipped with a mechanical stirrer, was prepared 2.86 moles of sodamide by slowly adding 65.78 g of sodium to about 700 mL of liquid ammonia containing a catalytic amount of ferric nitrate hexahydrate. The ammonia was substantially evaporated and replaced with 300 mL of toluene containing 0.1 mL of oleic acid. Monoethanolamine (0.1 mole) was added to the $NaNH_2$/toluene slurry while stirring. The mixture was transferred from the flask to a one liter autoclave, using 100 mL of toluene to rinse the flask.

The autoclave (available from Hazard Evaluation Laboratories, Limited) was equipped with automated controls for temperature, pressure, and stirring, and also with automated aquisition for temperature, pressure, stirring, and gas evolution via computer interface.

The autoclave was first purged of air with nitrogen and pressurized to 45 psig with $NH_3$ and further to 100 psig with $N_2$. The reactor was then heated to the reaction temperature of 150° C. and sufficient time provided to allow both the oil and reactor temperatures to reach a steady state condition. During this time the reactor pressure was increased to 350 psig with $N_2$.

The 3-methylpyridine was then added at a rate of 20 g/min until 190.2 g (2.04 mole) of feed had been added. The reaction was then allowed to proceed while maintaining the reactor temperature at 150° C. and the pressure at 350 psig. The reaction is exothermic. The reaction was determined to be complete when the rate of gas evolution became essentially zero. The reactor was then cooled and vented to 150 psig.

The reaction mixture was carefully hydrolyzed with 320 g water at 25°–30° C. and at 150 psig. The reactor was then vented to atmospheric pressure.

The two layers were then separated. The aqueous layer was extracted with an additional 25–40 mL toluene and the organic layers combined. The organic layer was distilled in order to remove the toluene and any low boiling organic materials. The resulting solvent cut and concentrated aminopyridines were then sampled for GC analysis. The concentrate which remained after solvent removal can be further distilled to obtain the isolated 2-amino-5-lower alkyl pyridine and 2-amino-3-lower alkyl pyridine mixture and a residue.

Results from the reaction are shown in Table 1, and demonstrate that the MEA additive gave a higher 2-amino-5-methylpyridine yield and went to completion significantly faster than a similarly-conducted reaction containing no additive (Example 2). The MEA was found to decrease the overall reaction time by about 55% compared to the reaction containing no catalyst. MEA was also found to increase the 2,5-:2,3- isomer ratio from 2.90 to 4.04. The decrease in reaction time while increasing both the 2,5- isomer yield and the 2,5-:2,3- isomer ratio provide substantial advantages in the aminations and illustrates the importance of the applicants' discoveries.

TABLE 1

| Example # | 1 | 2 |
|---|---|---|
| Starting Materials | | |
| mol NaNH2 | 2.86 | 2.86 |
| mol 3-Pic | 2.04 | 2.04 |
| mol 2A5 | 0 | 0 |
| Solvent/Vol | Tol/400 mL | Tol/400 mL |
| Remarks | 0.1 mol MEA | No Additives |
| Reaction Conditions | | |
| Reactor Size | 1.0 L | 1.0 L |
| Pressure | 350 psig | 350 psig |
| NH3 Press | 45 psig | 45 psig |
| Temp | 150° C. | 150° C. |
| Component Yields | | |
| 2A3 | 16.5 | 20.7 |
| 2A5 | 66.8 | 60.0 |
| Data Summary | | |
| % Conversion | 99.3 | 99.8 |
| 2A5/2A3 | 4.99 | 5.41 |
| Hydrogen Flow Total Rxn T | 150 | 330 |

EXAMPLES 3–10

Aminations of 3-picoline Under Varying Conditions

A series of experiments was performed to characterize the effects of MEA under varying reaction conditions. The scope of the study included presence of 2-amino-5-methylpyridine (2A5), temperature effects, partial pressure of $NH_3$, and MEA concentrations.

1. Effect of MEA and 2A5 as Co-Additives (Examples 3–4).

Experiments were conducted to examine the effect of 2A5 and MEA when combined, as compared to using either individually. The reactions for Examples 3 and 4 (Table 2) were performed as in Example 1 except 0.1 mole 2-amino-5-methylpyridine was added as a co-additive to the system (Example 3) or used alone (Example 4).

The results presented in Table 2 show that the exotherm in reactions using both 2A5 and MEA were completed much more quickly than the reaction using only MEA, 2A5 or no catalyst at all. The overall reaction time is reduced by 13% as compared to MEA alone, The 2A5/MEA reactions were found to increase the 2A5 yields from 66.8% to 71.4% and also increase the isomer ratio from 4.04 to 4.48.

TABLE 2

| Example # | 1 | 3 | 4 |
|---|---|---|---|
| Starting Materials | | | |
| mol NaNH2 | 2.86 | 2.86 | 2.86 |
| mol 3-Pic | 2.04 | 2.04 | 2.04 |
| mol 2A5 | 0.000 | 0.100 | 0.100 |
| Solvent/Vol | Tol/400 mL | Tol/400 mL | Tol/400 mL |
| Remarks | 0.1 mol MEA | 0.1 mol MEA | No MEA |
| Reaction Conditions | | | |
| Reactor Size | 1.0 L | 1.0 L | 1.0 L |
| Pressure | 350 psig | 350 psig | 350 psig |
| NH3 Press | 45 psig | 45 psig | 45 psig |
| Temp | 150° | 150° | 150° |
| Component Yields (%) | | | |
| 2A3 | 16.5 | 15.9 | 19.3 |
| 2A5 | 66.8 | 71.4 | 61.2 |
| Data Summary | | | |
| % Conversion | 99.3 | 99.5 | 99.7 |
| 2A5/2A3 | 4.04 | 4.48 | 3.17 |
| Hydrogen Flow Total Rnx T | 150 | 130 | 165 |

An additional discovery was that the usage of MEA causes the reaction mixture to be much less colored after hydrolysis. Additionally, the layer separation after hydrolysis proceeded much more quickly and readily as there was less of a emulsion/particulate layer formed.

2. Temperature/Ammonia Pressure Study (Examples 5–7).

Experiments were conducted to examine the effect of temperatures and partial pressures of NH3 on the reaction. All of the reactions were performed as in Example 1 with 0.1 mole 2A5 added as co-additive. The results are presented in Table 3. The results show that the reaction times are increased when either the ammonia pressure is increased or the temperature decreased. Even so the observed reaction times are equivalent to or improved versus the reaction performed without any additive. The 2,5-:2,3- ratio is improved with increasing ammonia concentration or decreasing reaction temperature. The yields for the various conditions studied were comparable. These examples illustrate that variations in the temperature and ammonia pressure can be made while still maintaining the described advantages.

TABLE 3

| Example # | 3 | 5 | 6 | 7 |
|---|---|---|---|---|
| Starting Materials | | | | |
| mol NaNH2 | 2.86 | 2.86 | 2.86 | 2.86 |
| mol 3-Pic | 2.04 | 2.04 | 2.04 | 2.04 |
| mol 2A5 | 0.100 | 0.100 | 0.100 | 0.100 |
| Solvent/Vol | Tol/400 mL | Tol/400 mL | Tol/400 mL | Tol/400 mL |
| Remarks | 0.1 mol MEA | 0.1 mol MEA | 0.1 mol MEA | 0.1 mol MEA |
| Reaction Conditions | | | | |
| Reactor Size | 1.0 L | 1.0 L | 1.0 L | 1.0 L |
| Pressure | 350 psig | 350 psig | 350 psig | 350 psig |

TABLE 3-continued

| Example # | 3 | 5 | 6 | 7 |
|---|---|---|---|---|
| NH3 Press | 45 psig | 45 psig | 45 psig | 100 psig |
| Temp | 150° | 137° | 132° | 137° |
| Component Yields | | | | |
| 2A3 | 15.9 | 13.8 | 12.8 | 12.2 |
| 2A5 | 71.4 | 68.7 | 69.4 | 69.7 |
| Data Summary | | | | |
| % Conversion | 99.5 | 99.3 | 98.6 | 98.8 |
| 2A5/2A3 | 4.48 | 4.99 | 5.41 | 5.71 |
| Hydrogen Flow Total Rxn T | 130 | 260 | 350 | 275 |

3. MEA Concentration (Examples 8–10).

A series of experiments was performed to examine the effect of MEA concentration on the reaction. The reactions were carried out as in Example 1 but with and without the presence of 2A5 in the system, and the results are presented in Table 4. Examination of the results from Example 8, which did not use 2A5 as a co-additive, shows that doubling the MEA concentration does not affect the improved reaction times. While the 2,5-:2,3- isomer ratio was improved a decrease in 2A5 yield was observed. Examination of the results from Examples 3, 9 and 10, which used 2A5 as a co-additive, shows that the improved reaction times are maintained when using increased or decreased concentrations of MEA. A variation in the 2,5-:2,3- isomer ratio was observed with improved ratios being obtained when doubling the MEA concentration. The 2A5 yields, within the concentrations examined, were comparable. Thus, variation in the amount of MEA employed can be made while still maintaining the described advantages.

TABLE 4

| Example # | 3 | 8 | 9 | 10 |
|---|---|---|---|---|
| Starting Materials | | | | |
| mol NaNH2 | 2.86 | 2.86 | 2.86 | 2.86 |
| mol 3-Pic | 2.04 | 2.04 | 2.04 | 2.04 |
| mol 2A5 | 0.1000 | 0.000 | 0.100 | 0.100 |
| Solvent/Vol | Tol/400 mL | Tol/400 mL | Tol/400 mL | Tol/400 mL |
| Remarks | 0.1 mol MEA | 0.2 mol MEA | 0.2 mol MEA | 0.04 mol MEA |
| Reaction Conditions | | | | |
| Reactor Size | 1.0 L | 1.0 L | 1.0 L | 1.0 L |
| Pressure | 350 psig | 350 psig | 350 psig | 350 psig |
| NH3 Press | 45 psig | 45 psig | 45 psig | 45 psig |
| Temp | 150° | 150° | 150° | 150° |
| Component Yield (%) | | | | |
| 2A3 | 15.9 | 13.8 | 13.7 | 18.6 |
| 2A5 | 71.4 | 58.5 | 67.2 | 68.8 |
| Data Summary | | | | |
| % Conversion | 99.5 | 98.5 | 97.1 | 99.8 |
| 2A5/2A3 | 4.48 | 4.24 | 4.91 | 4.48 |
| Hydrogen Flow Total Rxn T | 130 | 155 | 130 | 125 |

EXAMPLE 11

Amination of Niacin 120 cc toluene containing 0.06 cc oleic acid, 18.45 g (ca 0.15 moles) of USP grade niacin, and 15.2 g (0.350 moles) of 90% $NaNH_2$ (Aldrich Chemical) were charged to a 300 ml PARR Autoclave reactor. For the MEA catalyzed reaction 0.46 g MEA (5 molar % to niacin) was added to the toluene/oleic acid mixture prior to addition to the autoclave body. The Autoclave was then purged three (3) times with $N_2$. The autoclave was depressurized and $NH_3$ was added to maintain ca 32 psig pressure in the autoclave. $N_2$ was added to increase pressure to a total of 200 PSIG. With agitation the autoclave was heated to reaction temperature at which time additional nitrogen was added to give 350 psig. As the amination reaction proceeded hydrogen gas was released through the regulator and quantitated. After the reaction gas evolution subsided, the temperature was increased to 165° C., little to no additional gas evolution was observed for both runs at the elevated temperature. The reaction mixture was cooled to 25° C., gas pressure vented, and carefully hydrolyzed with 45 g of water keeping the hydrolysis temperature below 50° C. The two layers were then separated. After analysis of the aqueous layer by titration the aqueous layer was adjusted to pH's of 8.2, 6.0, and 3.85, and the precipitated solids were filtered, rinsed with minimal $H_2O$, and dried. The solids were analyzed by melting point, IR and NMR. Similar products were formed in both the MEA and non MEA catalyzed aminations. For the non MEA catalyzed amination the yield of 6-aminonicotinic acid (6.4 g) and 2.6-diaminonicotinic acid (2.6 g) were 13.3% and 4.8% respectively. For the MEA catalyzed amination the yield of 6-aminonicotinic acid (7.5 g) and 2.6-diaminonicotinic acid (1.7 g) were 15.6% and 3.1% respectively. The MEA catalyzed run was essentially finished at 30 minutes, whereas the non-MEA catalyzed run required 95 minutes to finish. The MEA improved the yield of 6-aminonicotinic acid and significantly improved the reaction rate.

EXAMPLE 12

Amination of 4-(5-nonyl) Pyridine

In a 1-liter 3-neck flask equipped with a mechanical stirrer, 0.41 moles of $NaNH_2$ was prepared by sodium addition (0.41 moles) to ferric nitrate catalyzed liquid $NH_3$. 250 cc of mixed xylenes containing 0.25 cc oleic acid was added to the mixture to displace the $NH_3$. The resulting sodium amide slurry was heated under a nitrogen blanket to reflux. The nonylpyridine was then added over a 10 minute period. The reaction mixture was held at reflux until the gas evolution was essentially zero. Gas evolution was monitored by gas bubble evolution through mineral oil trap. For the MEA catalyzed amination, MEA (1.49 g, 5 molar % to nonylpyridine) was added to the refluxing $NaNH_2$/toluene slurry prior to nonylpyridine addition. The reaction mixture was hydrolyzed with 45 cc of $H_2O$ added at reflux. The hydrolyzed reaction mixture was cooled and the two layers separated. The organic layer was distilled through a vigeroux column to a maximum of 295° C./1.5 mm Hg pressure. The distillate cuts and residue were analyzed by GC. For the non-MEA catalyzed amination a yield, based on 4-(5-nonyl) pyridine consumed, of 14.3% for 2-Amino-4-(5-nonyl) pyridine was obtained. The MEA catalyzed run gave an improved yield, based on 4-(5-nonyl) pyridine consumed, of 28.5% for 2-Amino-4-(5-nonyl) pyridine. In addition, the MEA catalyzed amination run was complete in ½ the reaction time of the non MEA catalyzed run (ca 1 ½ hours vs. 3 hours for the non-MEA catalyzed run).

EXAMPLE 13

Amination of Quinoline

To a 300 mL Parr autoclave was charged 19.5 g of 90% solid NaNH$_2$ (0.45 mole). To this was added 100 mL toluene and 6 drops of oleic acid. The vessel was then sealed and purged with nitrogen. The reactor was then pressurized to 150 psig and simultaneously heated to 140° C. Quinoline (0.25 mole) was then charged to the reactor initially at a rate of 3 mL/min and then to 2 mL/min after a few minutes of addition. The reactor was held at 140° C. for 3.5 hours (150 psig). The reactor was cooled to room temperature for hydrolysis. After washing the feed lines with toluene, methanol, and water, the lines were primed with water, and 50 g of water was pumped into the reactor at a rate of 5.0 mL/min to hydrolyze the reaction mixture. For workup, solids were filtered from the organic layer from the hydrolysis mixture following the removal of the aqueous layer. These solids were washed with toluene which was added to the mother liquor. The solids were then dried in a vacuum oven overnight. The aqueous layer was extracted with toluene. The combined organic layers and solids were analyzed by GC and GC/MS. Similar products were obtained for the MEA catalyzed and non-MEA catalyzed aminations. For the non-MEA catalyzed reaction the yield of 2-aminoquinoline (10.7 g) and 2-amino-3,4-dihydroquinoline (14.7 g) were 29.8% and 40.4% respectively. For the MEA catalyzed reaction the yield of 2-aminoquinoline (12.7 g) and 2-amino-3,4-dihydroquinoline (16.6 g) were 35.3% and 45.4% respectively. An improvement in yields for both of these compounds was observed for the MEA catalyzed reaction.

EXAMPLE 14

Amination of Pyridine

Sodium amide was prepared in a 1.0 L 3 neck flask using 25.30 g (1.10 mole) solid Na and 1.25 g ferric nitrate catalyst in liquid NH$_3$ to form 1.10 mole NaNH$_2$. The liquid ammonia was solvent exchanged with 300 mL toluene that contained 1.0 mL oleic acid which was then heated to reflux for one hour. Upon cooling the NaNH$_2$ slurry was transferred to a autoclave as in Example 1 above with the aid of an additional 100 mL toluene as wash. The autoclave was then sealed and purged with nitrogen and pressurized with nitrogen. For the MEA catalyzed reaction, 3.06 g (0.05 mole) MEA was added via pipette to the cool NaNH$_2$ prior to transfer to the autoclave. The reactor was then depressurized, pressurized to 150 psig with N$_2$ and heated to 125° C. while maintaining a 150 psig pressure. 79.1 g (1.0 mole) pyridine was added at 10 g/min and the reaction allowed to proceed isothermally at 125° C. and about 150 psig. The reaction was determined to be complete when the gas evolution had subsided. The reactor was then cooled for hydrolysis. The cooled reaction was hydrolyzed using 123 g H$_2$O. The hydrolysis temperature never exceeded 80° C. (150 psig) during these operations. The hydrolyzed reaction mixture was cooled and removed from the reactor. The layers were separated and the aqueous phase extracted twice with 30–40 mL aliquots of toluene. The layers were separated after each extraction and the organic portions combined. The organics were then distilled at atmospheric conditions to concentrate the 2-aminopyridine and analyzed by GC. The standard reactions (without MEA) were similarly run at a reaction temperature of 125° C. and a pressure of 150. The results showed the time of reaction was greatly reduced with the use of MEA as an additive, decreasing from approximately 500 minutes down to 220 minutes when MEA was used.

EXAMPLES 16–73

In these examples a wide variety of additives were evaluated for their ability to favorably influence Chichibabin aminations. Procedurally, the methods described for Example 1 above were repeated, except in each case using the additive identified in Table 5 below. As the results demonstrate, the applicants have discovered a broad range of additives for improving the amination of pyridine bases, particularly for example wherein the additives significantly decrease the duration required to complete the reaction.

TABLE 5

| Additive | Ex. | Yield 2A3 | Yield 2A5 | Convers | 2A5/2A3 | H2 end T |
|---|---|---|---|---|---|---|
| None | 16 | 20.7 | 60.0 | 99.8 | 2.90 | 330 |
| 2A5 | 17 | 19.3 | 61.2 | 99.7 | 3.17 | 165 |
| Aniline | 18 | 20.6 | 67.6 | 99.8 | 3.27 | 170 |
| 3-MethylPiperidine | 19 | 22.4 | 62.9 | 99.9 | 2.80 | 330 |
| 1-PhenylPiperidine | 20 | 22.9 | 62.9 | 99.9 | 2.74 | 300 |
| 3-methylcyclopentanone | 21 | 22.4 | 66.3 | 99.6 | 2.95 | 230 |
| Phenol | 22 | 20.4 | 68.9 | 99.8 | 3.38 | 260 |
| 18-Crown-6 Ether | 23 | 18.8 | 63.3 | 99.7 | 3.36 | 235 |
| Dytek Diamine | 24 | 21.8 | 67.6 | 99.8 | 3.10 | 260 |
| 2-AminoEthanol (MEA) | 25 | 16.5 | 66.8 | 99.3 | 4.04 | 150 |
| 2A5/MEA | 26 | 15.0 | 69.8 | 99.6 | 4.64 | 125 |
| EthyleneDiamine | 27 | 18.0 | 68.9 | 99.8 | 3.83 | 130 |
| t-Butanol | 28 | 20.8 | 66.5 | 99.9 | 3.20 | 185 |
| DiethanolAmine | 29 | 17.0 | 67.6 | 98.2 | 3.97 | 150 |
| Melamine | 30 | 19.7 | 67.0 | 99.2 | 3.40 | 185 |
| N,N-DimethylAniline | 31 | 22.3 | 61.4 | 99.8 | 2.75 | 190 |
| 3-Amino-1-Propanol | 32 | 20.8 | 63.1 | 99.6 | 3.04 | 85 |
| 2-AminoPhenol | 33 | 21.8 | 68.0 | 99.7 | 3.12 | 145 |
| n-Butanol | 34 | 22.0 | 66.9 | 99.8 | 3.05 | 155 |
| n-ButylAmine | 35 | 21.0 | 66.7 | 99.8 | 3.18 | 185 |
| 4-Amino-1-Butanol | 36 | 20.7 | 66.1 | 99.7 | 3.19 | 120 |
| 2A3 | 37 | 22.6 | 65.1 | 99.7 | 2.88 | 125 |
| Di-n-ButylAmine | 38 | 23.1 | 64.8 | 99.8 | 2.80 | 180 |
| Beta-Alanine | 39 | 21.3 | 68.6 | 99.5 | 3.23 | 165 |

TABLE 5-continued

| Additive | Ex. | Yield 2A3 | Yield 2A5 | Convers | 2A5/2A3 | H2 end T |
|---|---|---|---|---|---|---|
| 4-Amino-Butyric Acid | 40 | 19.0 | 67.2 | 99.5 | 3.52 | 120 |
| 3-Methoxy-Propylamine | 41 | 19.0 | 70.2 | 99.8 | 3.70 | 135 |
| Ethylene Glycol Dimethyl Ether | 42 | 18.5 | 66.9 | 99.4 | 3.62 | 260 |
| DMSO | 43 | 17.4 | 65.0 | 98.5 | 3.74 | 245 |
| HMPA | 44 | 19.9 | 71.1 | 99.7 | 3.57 | 170 |
| 2-PyridylCarbinol | 45 | 20.5 | 68.2 | 99.8 | 3.32 | 130 |
| 2-HydroxyPyridine | 46 | 20.3 | 68.2 | 99.8 | 3.35 | 145 |
| 1,2-DimethoxyBenzene | 47 | 22.8 | 66.0 | 99.8 | 2.89 | 175 |
| Tetrahydrofuran | 48 | 21.9 | 65.8 | 99.8 | 3.01 | 165 |
| trans1,2-Diaminocyclohexane | 49 | 21.3 | 65.9 | 99.6 | 3.10 | 185 |
| 2-(2-aminoethoxy)ethanol | 50 | 17.4 | 65.9 | 99.6 | 3.78 | 190 |
| 1-Amino-2-Propanol | 51 | 17.7 | 66.3 | 99.3 | 3.75 | 145 |
| Benzophenone | 52 | 22.1 | 65.5 | 99.8 | 2.96 | 185 |
| N,N-Dimethyl Formamide | 53 | 18.5 | 66.3 | 99.7 | 3.59 | 190 |
| 2-PyridylCarbinol/ 3-MethoxyPropylAmine | 54 55 | 20.4 | 68.6 | 99.3 | 3.35 | 85 |
| Methane Sulfonic Acid | 56 | 23.0 | 64.4 | 99.7 | 2.80 | 185 |
| Cumene | 57 | 22.3 | 63.9 | 99.8 | 2.86 | 180 |
| NitroBenzene | 58 | 21.0 | 68.1 | 99.4 | 3.24 | 155 |
| 1-EthanolPiperidine | 59 | 22.5 | 67.1 | 99.6 | 2.98 | 150 |
| Tetra Methyl Ammonium Acetate | 60 | 21.1 | 66.2 | 99.6 | 3.14 | 205 |
| 1-Hexyne | 61 | 26.6 | 60.0 | 99.6 | 2.25 | 205 |
| 2-(Butylamino)Ethanethiol | 62 | 19.1 | 67.3 | 98.8 | 3.52 | 165 |
| 2-(2-aminoethylamino)-5-Nitropyridine | 63 | 14.9 | 65.2 | 95.5 | 4.36 | 300 |
| 2-PyridylCarbinol/ 3-MethoxyPropylAmine | 64 65 | 20.4 | 68.6 | 99.3 | 3.35 | 85 |
| n-Butanol/THF | 66 | 19.9 | 59.6 | 99.6 | 2.99 | 170 |
| 2A5/t-Butanol | 67 | 21.1 | 65.3 | 99.6 | 3.10 | 115 |
| n-Butylamine/Melamine | 68 | 20.0 | 67.1 | 99.3 | 3.35 | 195 |
| 1-Amino-2-Propanol/HMPA | 69 | 16.2 | 65.0 | 96.2 | 4.01 | 155 |
| 2-Hydroxypyridine/ EthyleneDiamine | 70 | 16.7 | 68.7 | 99.3 | 4.11 | 115 |
| Aniline/HMPA | 71 | 19.5 | 69.0 | 99.7 | 3.54 | 140 |
| 2A3/n-Butanol | 72 | 20.5 | 63.1 | 99.6 | 3.08 | 120 |
| 2A5/MEA | 73 | 15.0 | 69.8 | 99.6 | 4.64 | 125 |

All references cited herein are illustrative of the level of skill in the art and are hereby incorporated herein by references as if each had been individually incorporated by reference and fully set forth.

While the invention has been illustrated and described in detail in the foregoing description, the same is to be considered as illustrative and not restrictive in character, it being understood that only the preferred embodiment has been described and that all changes and modifications that come within the spirit of the invention are desired to be protected.

What is claimed is:

1. An improved Chichibabin amination which comprises:

reacting a reaction mixture containing an organic solvent, a pyridine base, sodamide, and an organic additive compound which increases the rate of said reacting and is encompassed by the formula:

I wherein X is S, O, $NR^3$, or $CO_2$ wherein $R^1$, $R^2$ and $R^3$ are H, alkyl, aryl, or aralkyl, and n is 0 to about 12;

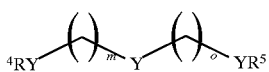

II wherein Y is O, S, or $NR^6$, $R^4$, $R^5$ and $R^6$ are H, alkyl, aryl, or aralkyl, and m and o are 1 to about 12;

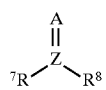

III wherein Z is C or S, A is O or $NR^9$, and $R^7$, $R^8$ and $R^9$ are H, alkyl, aryl or aralkyl;

$$^{10}R—B$$  IV wherein B is $OR^{11}$, $CR^{11}$, $NR^{12}R^{13}$, $SR^{14}$, $CO_2R^{15}$, $NO_2$ or CN, $R^{10}$ is alkyl, and $R^{11}$, $R^{12}$, $R^{13}$, $R^{14}$ and $R^{15}$ are H, alkyl, aryl or aralkyl;

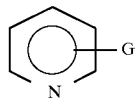

V wherein G is $—OR^{16}$, $—ROR^{17}$ or $NR^{22}R^{23}$ wherein $R^{16}$ and $R^{17}$ are H or alkyl and R, $R^{22}$ and $R^{23}$ are alkyl;

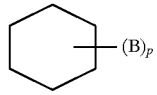

VI wherein B is as defined above and p is 1 to 4;

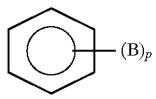

wherein B is as defined above and p is 1 to 4; or a cyclic ether or single electron transfer agent, so as to aminate said base.

2. The process of claim 1 wherein the organic additive is of formula I.

3. The process of claim 2 wherein n is 1 to 6 and wherein R1, R2 and R3 are H or lower alkyl.

4. The process of claim 1 wherein the organic additive is of formula II.

5. The process of claim 4 wherein R4, R5 and R6 are H or lower alkyl, and wherein at least one of m and n is at least 1.

6. The process of claim 1 wherein the organic additive is of formula III.

7. The process of claim 6 wherein R7, R8 and R9 are lower alkyl or phenyl, and wherein Z is C and A is O.

8. The process of claim 1 wherein the organic additive is of formula IV.

9. The process of claim 8 wherein R11, R12, R13, R14 and R15 are H or lower alkyl.

10. The process of claim 1 wherein the organic additive is of formula V.

11. The process of claim 10 wherein R 16 and R17 are H or lower alkyl and R22 and R23 are lower alkyl.

12. The process of claim 1 wherein the organic additive is of formula VI.

13. The process of claim 12 wherein p is 2 and wherein the substituents B occur ortho to one another.

14. The process of claim 1 wherein the organic additive is of formula VII.

15. The process of claim 14 wherein p is 2 and wherein the substituents B occur ortho to one another.

16. The process of claim 1 wherein the organic additive is a cyclic ether.

17. The process of claim 1 wherein the organic additive is a single electron transfer agent.

18. The process of claim 1 wherein the organic additive is hexamethylphosphoramide.

19. The process of claim 1 wherein the organic additive is tetramethylammonium acetate.

20. The process of claim 1 wherein the organic additive is hexyne.

21. An improved Chichibabin amination which comprises:
  reacting a reaction mixture containing an organic solvent, a pyridine base, sodamide, and an organic additive compound encompassed by the formula: additive compound which increases the rate of said reacting and is encompassed by the formula:

wherein X is S, O, NR$^3$, or CO$_2$ wherein R$^1$, R$^2$ and R$^3$ are H, alkyl, aryl, or aralkyl, and n is 0 to about 12;

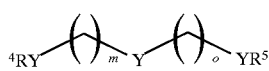

wherein Y is O, S, or NR$^6$, R$^4$, R$^5$ and R$^6$ are H, alkyl, aryl, or aralkyl, and m and o are 1 to about 12;

wherein Z is C or S, A is O or NR$^9$, and R$^7$, R$_8$ and R$^9$ are H, alkyl, aryl or aralkyl;

wherein B is OR$^{11}$, NR$^{12}$R$^{13}$, SR$^{14}$, CO$_2$R$^{15}$ NO$_2$ or CN, R$^{10}$ is alkyl, and R$^{11}$, R$^{12}$, R$^{13}$, R$^{14}$ and R$^{15}$ are H, alkyl, aryl or aralkyl;

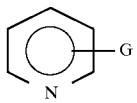

wherein G is —OR$^{16}$, —ROR$^{17}$ or NR$^{22}$R$^{23}$ wherein R$^{16}$ and R$^{17}$ are H or alkyl and R, R$^{22}$ and R$^{23}$ are alkyl;

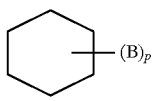

wherein B is as defined above and p is 1 to 4;

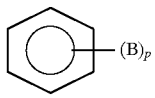

wherein B is as defined above and p is 1 to 4; or is a cyclic ether or single electron transfer agent, so as to aminate said base.

22. A process for producing 2-amino-5-lower alkyl pyridine, comprising:
  forming a solid-liquid heterogeneous reaction mixture containing a 3-lower alkyl pyridine, sodamide, a hydroxyalkylamine of the formula (R$^{18}$) (R$^{19}$)N—R$^{20}$ wherein R$^{18}$ and R$^{19}$ are —H, lower alkyl or lower hydroxyalkyl and R$^{20}$ is lower hydroxyalkyl, and an organic solvent;
  reacting the reaction mixture and, during said reacting, providing an ammonia-containing gas phase at superatmospheric pressure above the reaction mixture; and
  hydrolyzing the reacted reaction mixture to produce 2-amino-5-lower alkyl pyridine.

23. The process of claim 22 wherein said forming also includes incorporating an amino-lower alkyl pyridine in the reaction mixture.

24. The process of claim 23 wherein the 3-lower alkyl pyridine is 3-methylpyridine and said forming includes incorporating 2-amino-5-methylpyridine in the reaction mixture.

25. The process of claim 24 wherein said reacting is at a temperature of about 100° C. to about 250° C., and said hydroxyalkylamine is monoethanolamine.

26. The process of claim 25 wherein the ammonia-containing gas phase is at a pressure of at least 50 psig at the initiation of said reacting.

27. A process for increasing the rate of reaction in a Chichibabin amination of a 3-lower alkyl pyridine to form a mixture of 2-amino-3-lower alkyl pyridine and 2-amino-5-lower alkyl pyridine, comprising:
  conducting the Chichibabin amination in a heterogeneous reaction mixture containing sodamide, 3-lower alkyl pyridine, a hydroxyalkylamine of the formula $(R^{18})(R^{19})N—R^{20}$ wherein $R^{18}$ and $R^{19}$ are —H, lower alkyl or lower hydroxyalkyl and $R^{20}$ is lower hydroxyalkyl, and an organic solvent; and wherein during said conducting the reaction mixture is exposed to an ammonia-containing gas phase at superatmospheric pressure.

28. The process of claim 27 wherein at the initiation of the Chichibabin amination the heterogeneous reaction mixture further comprises a 2-amino-5-lower alkyl pyridine and the gas phase contains a partial pressure of ammonia of at least about 5 psig.

29. The process of claim 28 wherein $R^{18}$ and $R^{19}$ are —H.

30. The process of claim 29 wherein the hydroxyalkylamine is monoethanolamine.

31. The process of claim 30 wherein the organic solvent is toluene or xylene.

* * * * *

UNITED STATES PATENT AND TRADEMARK OFFICE
CERTIFICATE OF CORRECTION

PATENT NO : 5,808,081
DATED : September 15, 1998
INVENTOR(S): Phillip B. Lawin et al.

It is certified that error appears in the above-identified patent and that said Letters Patent is hereby corrected as shown below:

In col. 18, line 6, please delete "$R_8$" and insert in lieu thereof --$R^8$--.

Signed and Sealed this

First Day of June, 1999

Q. TODD DICKINSON

Attest:

Attesting Officer

Acting Commissioner of Patents and Trademarks